United States Patent [19]
Utecht

[11] Patent Number: 5,862,916
[45] Date of Patent: Jan. 26, 1999

[54] PERSONAL PROTECTION APPARATUS

[76] Inventor: Leo J. Utecht, 9905 Hamilton Rd., Eden Prairie, Minn. 55344

[21] Appl. No.: 869,650

[22] Filed: Jun. 5, 1997

Related U.S. Application Data

[63] Continuation-in-part of Ser. No. 733,127, Oct. 17, 1996, abandoned, which is a continuation of Ser. No. 85,724, Jul. 6, 1993, abandoned.

[51] Int. Cl.$^6$ .................................................. B65D 69/00
[52] U.S. Cl. ........................... 206/570; 206/278; 206/438
[58] Field of Search ................................... 206/278, 438, 206/570; 2/159; 15/227; 294/1.3

[56] References Cited

U.S. PATENT DOCUMENTS

| | | | |
|---|---|---|---|
| 3,608,708 | 9/1971 | Storandt | 15/227 |
| 4,169,550 | 10/1979 | Williams | 206/570 |
| 5,207,303 | 5/1993 | Oswalt et al. | 206/570 |
| 5,301,806 | 4/1994 | Olson | 206/278 |

*Primary Examiner*—Jim Foster
*Assistant Examiner*—Jermie E. Cozart
*Attorney, Agent, or Firm*—James E. Brunton

[57] ABSTRACT

A compact, easy-to-carry and easy-to-use accident victim emergency kit which includes the essential items necessary to provide emergency treatment to accident victims. The kit is in the nature of a fold-out-type apparatus which includes a number of personal protection treatment devices including a specially designed treatment mit that effectively protects the patient and the care giver as well as bystanders and clean-up personnel from exposure to hazardous material of the character often encountered when medical care is provided at accident sites and in emergency situations.

17 Claims, 4 Drawing Sheets

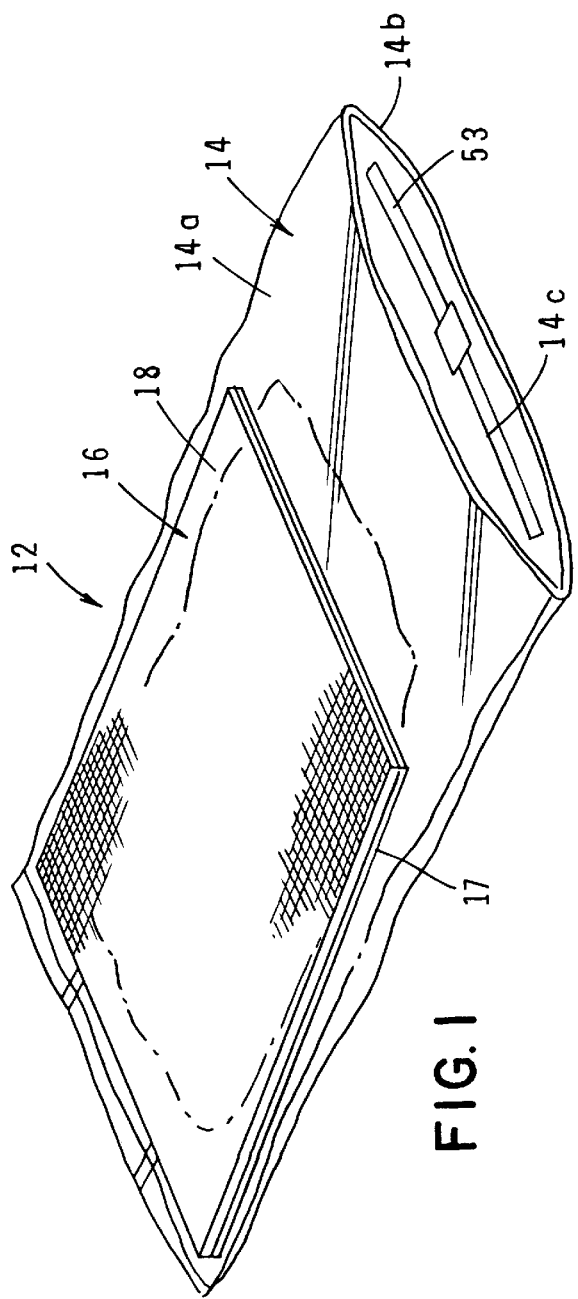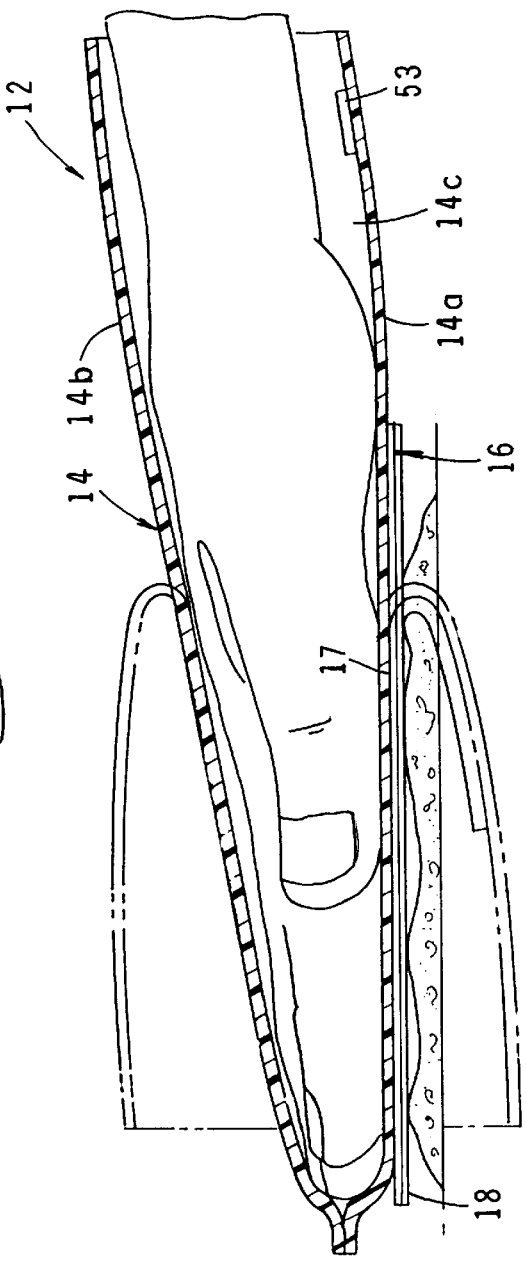

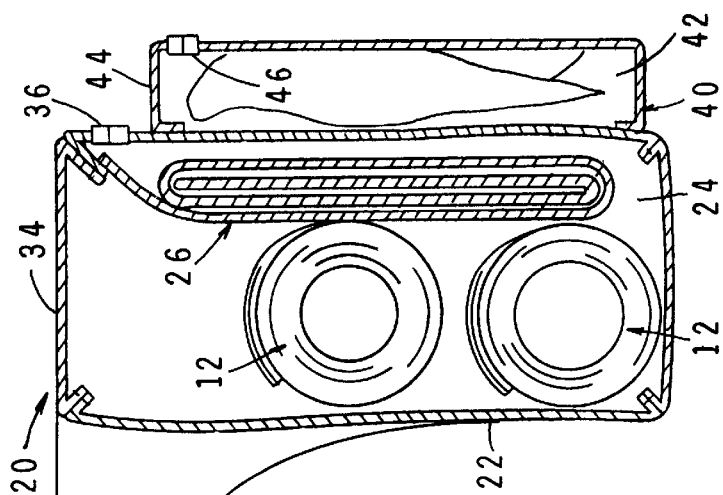
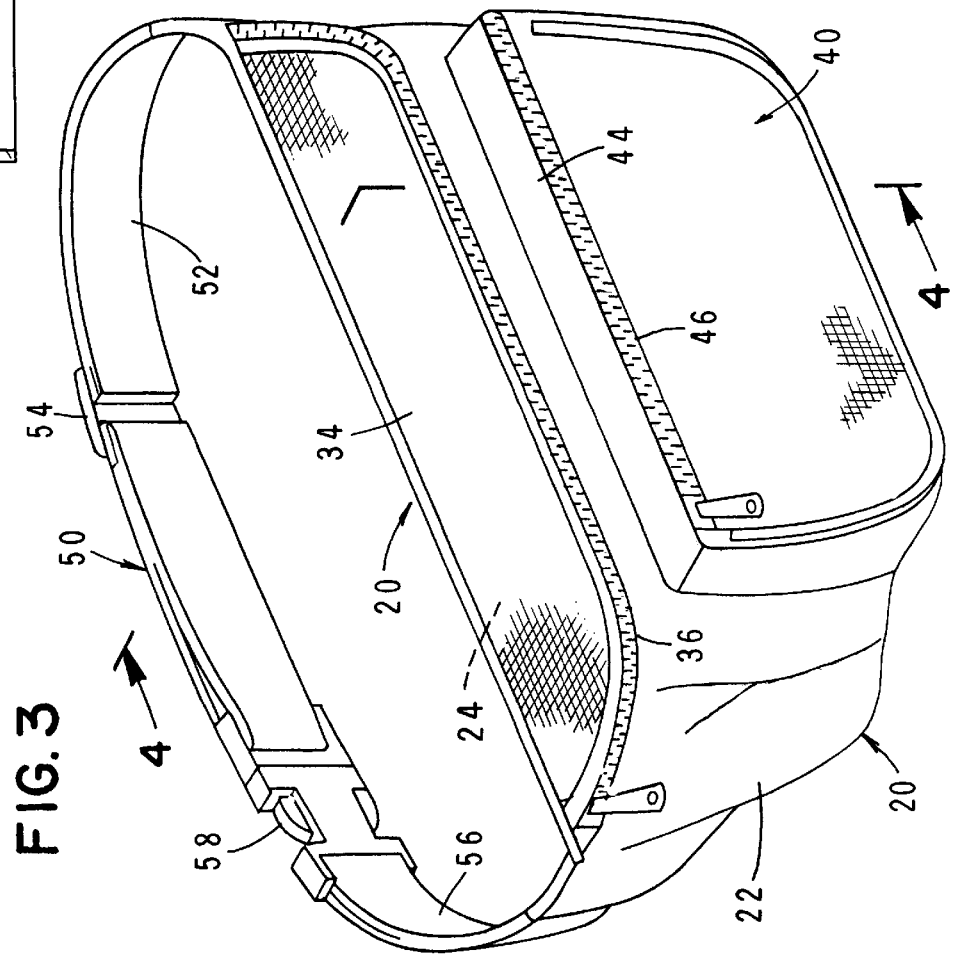

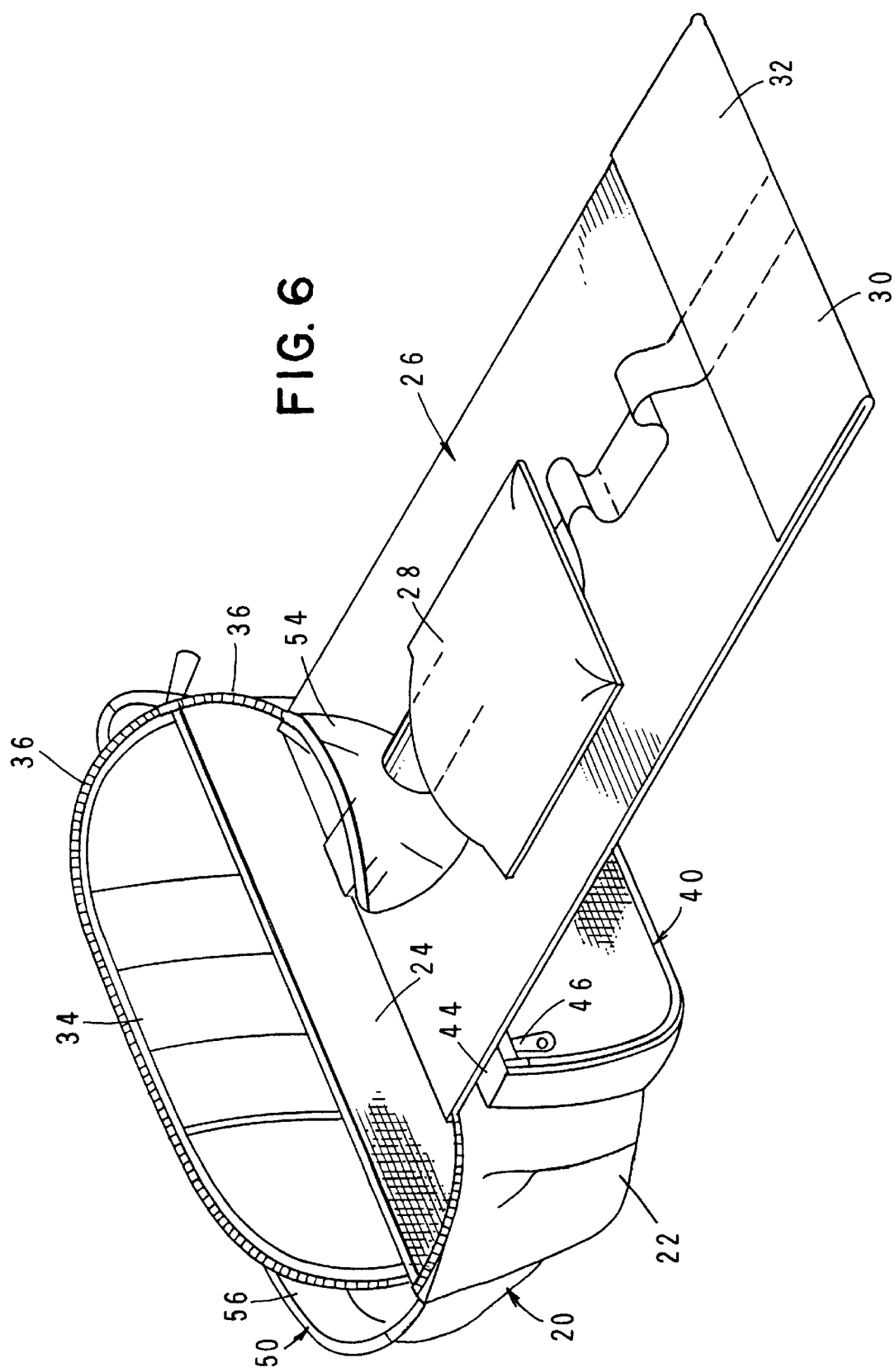

PERSONAL PROTECTION APPARATUS

BACKGROUND OF THE INVENTION

This is a Continuation-In-Part of application, Ser. No. 08/733,127 filed Oct. 17, 1996, abandoned, which is a Continuation of application, Ser. 08/085,724 filed Jul. 6, 1993, and now abandoned.

FIELD OF THE INVENTION

The present invention relates generally to infection control and personal protection devices provided in a novel kit form. More particularly, the invention concerns a compact, first-aid-type kit which contains various infection control, personal protection and injury treatment items, including novel glove-like devices that can be conveniently used for the cleanup, containment and disposal of infectious and hazardous materials

DISCUSSION OF THE INVENTION

In recent years, there has been an ever increasing need for new and innovative methods and devices for use in providing emergency aid to accident victims while at the same time protecting the care giver from direct contact with dangerous materials capable of spreading infectious diseases. More particularly, the need has grown in direct proportion to the public's expanding knowledge that infectious diseases such as AIDS and Hepatitis "B" can be contracted not only from direct contact with an infected person but also from indirect contact through exposure to contaminated materials used in the treatment of infected persons.

In the last year alone, statistics reveal that there have been many thousands of cases of infectious disease transfer between patients and medical care givers. These substantial problems and the prior art attempts to deal with them are discussed in greater detail in co-pending U.S. application, Ser. No. 08/733,127, which application is hereby incorporated by reference as though fully set forth herein. As pointed out in this incorporated-by-reference application, in serious accident situations it is important to provide the care giver with various types of emergency treatment devices which are designed to remain with the patient rather than with the care giver. These emergency treatment items need to be relatively small so as to be convenient to carry, they need to be simple to use, and they need to be designed to provide positive protection to the care giver while at the same time enabling the adequate performance of initial treatment at the accident site. Importantly, the treatment and personal protection devices available to the care giver must effectively block the transfer of fluids, viruses, spores, bacteria, or microorganisms from the patient to the care giver, and at the same time must function in widely varying weather conditions. Further, they must enable prompt direct medical assistance to be provided to the patient and be appropriate for use in the treatment of a wide range of injuries.

While a number of types of so-called "first aid kits" have been suggested in the past, these prior art kits typically are incomplete and fail to give adequate consideration to providing necessary protection to the care giver and to the environment proximate the accident site. A number of the prior art devices, of which the inventor is aware, are discussed in greater detail in incorporated-by-reference application Ser. No. 08/733,127.

As will be better understood from the descriptions which follow, the unique design of the apparatus of the present invention gives to the care giver ready access to essential items needed to provide adequate emergency treatment, such as cardiopulmonary resuscitation (CPU) masks and gloves or protective mits of novel design which can be used by the care giver to apply a dressing to a wound in a manner so as to substantially avoid cross-contamination between the patient and the care giver. The apparatus accident-victim-emergency-treatment kit of the invention also uniquely permits containment clean-up and removal of a myriad of different types of unwanted and dangerous material without the danger of spread of contamination. After clean up, the novel protective mits apparatus of the invention also can be used to accomplish the safe transport of the contaminates to a final disposal site without risk of cross-contamination.

As will be better appreciated from the description that follows, the apparatus of the invention is compact, light weight and readily transportable. Further, it specially designed for use in the home, at sporting events or on the road and represents a significant step forward in the contamination-free treatment of accident victims.

In one form of the invention, the treatment apparatus comprises a novel fold-out kit that includes a mask for use in cardiopulmonary resuscitation, a supply of tape and bandages and one or more first-aid mits which are uniquely designed to permit the use of one or more hands of one or more individuals and also to provide means for safe containment and disposal of the mit after use. More particularly, the mits are designed so that after the treatment has been completed, the mit can be turned inside out to safely enclose the contaminants thereon.

SUMMARY OF THE INVENTION

A primary object of the present invention is to provide a compact, easy-to-carry and easy-to-use accident victim emergency treatment kit which includes the essential items necessary to provide emergency treatment to accident victims. More particularly, it is an object of the invention to provide a novel, easy-to-use, fold-out-type kit which includes a number of personal protection treatment devices that effectively protect the patient and the care giver as well as bystanders and clean-up personnel from exposure to hazardous material of the character often encountered when medical care is provided at accident sites and in emergency situations.

Another object of the invention is to provide an apparatus of the character described that provides the care giver quick and easy access to essential first-aid implements including a small CPR mask, a number of bandages and dressings and adhesive tape as well as the novel gloves or protective mits which can be used to treat the victim in a safe and contamination-free manner. More particularly, the novel protective units included in the emergency treatment kit prevent the transfer of blood and body fluids between the care giver and the patient while at the same time providing effective means for the control and containment of bleeding.

Another object of the invention is to provide a treatment kit of the class described in which the protective mits of the kit can be used for applying a sterile dressing in a manner that protects the entire hand of the care giver from any contact with any elements or microorganisms outside the protective exterior of the pouch, thereby preventing cross-contamination between patients, care givers, clothing and equipment.

Another object of the invention is to provide a novel emergency treatment kit which is self-contained, provides a convenient and substantially sterile transport medium for the various items and implements normally required in providing emergency first-aid treatment.

her objects of the invention are set forth in the incorporated by reference application Ser. No. 08/733,127.

BRIEF DESCRIPTION OF THE DRAWINGS

FIG. 1 is a generally perspective view of one form of the of the emergency treatment glove or mit of the present invention.

FIG. 2 is an enlarged, side-elevational, cross-sectional view of the mit shown in FIG. 1.

FIG. 3 is a generally perspective view of one form of the emergency treatment kit of the invention.

FIG. 4 is a cross-sectional view taken along lines 4—4 of FIG. 3.

FIG. 6 is a generally perspective view of the kit shown in FIG. 3, but showing the kit in a fold-out configuration.

DESCRIPTION OF THE INVENTION

Figure 5:
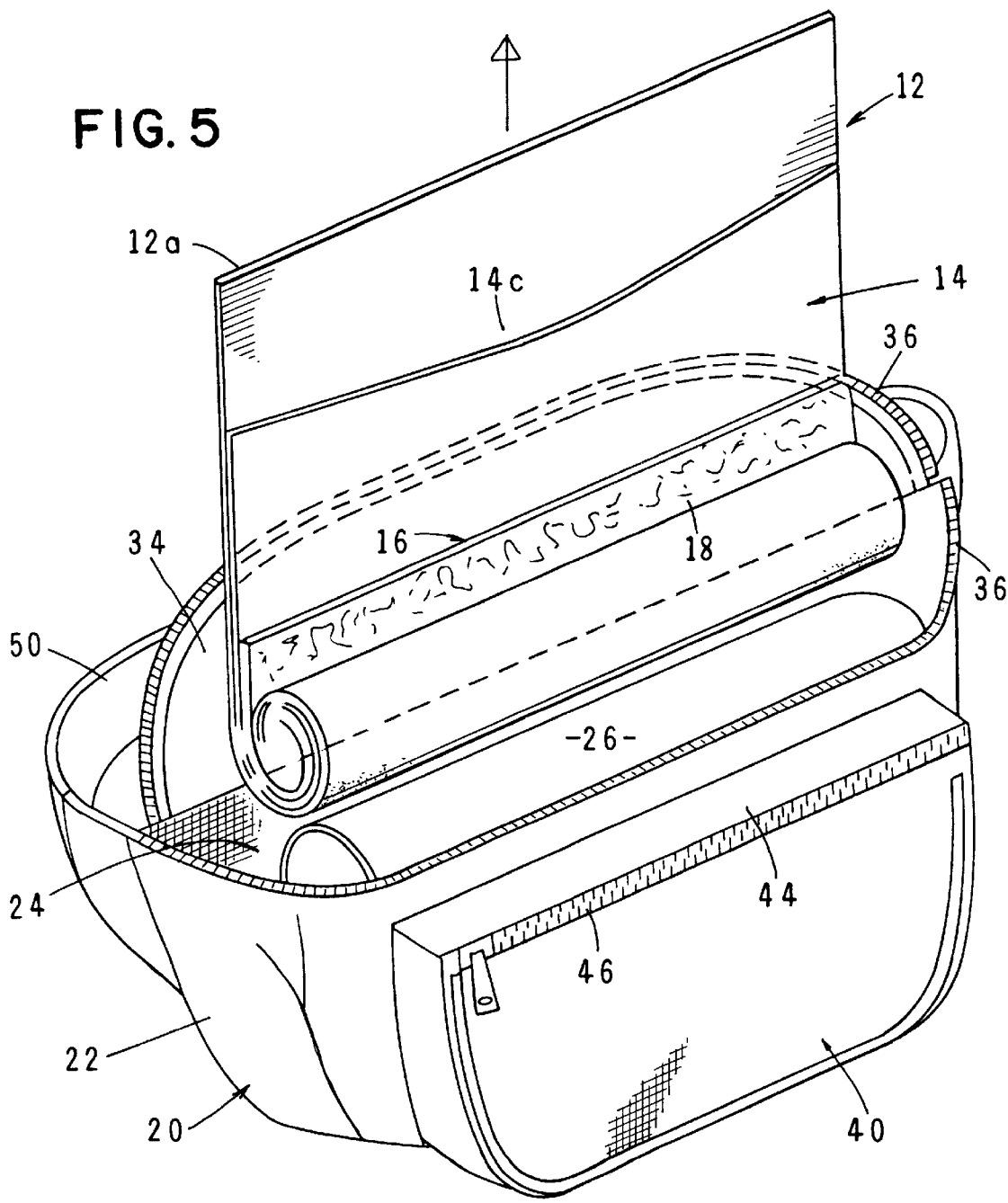
FIG. 5 is a generally perspective view of the kit shown in FIG. 3 but showing the kit in an open configuration with one of the protective units being withdrawn therefrom.

Referring to the drawings and particularly to FIGS. 3, 4, and 5 one form of the accident-victim-emergency-treatment kit of the invention is there shown. As previously mentioned, the kit contains a number of treatment items, the details of which will presently be described. Among these treatment items are the important combined treatment, clean-up, transport and disposal treatment mits of the invention. The manner in which these novel mits are stowed within the kit is illustrated in FIGS. 4 and 5 wherein the mits are generally designated by the numeral 12.

In the form of the invention shown in the drawings, each of the treatment mits comprises a barrier member 14 constructed from a thin film of microporous material that prohibits the passage therethrough of contaminants including infectious disease, micro-organisms, bacteria, viruses, spores and other hazardous contaminants.

As best seen in FIGS. 1 and 2, the barrier member, can take the shape of a pouch, a glove, a gauntlet or a mitten. Each barrier member 14 includes a front surface 14a and a back surface 14b which cooperate to define a hand receiving chamber 14c (FIG. 2). In one form of the invention, the barrier member 14 comprises a seamless, pouch-like enclosure which is free of pin holes and is constructed of a thin film of a suitable microporous, non-latex material that has pores smaller in size than 90 nanometers.

Affixed to the front surface, or face 14a of the barrier member, is engaging means for engagement with sources of contamination including burn areas, wound areas and contaminated surfaces of various kinds. The engaging means here comprises a plurality of discrete layers of material superimposed over one another. The various layers of the assemblage which comprises the engaging means are collectively identified in FIGS. 1 and 2 by the numeral 16. The individual layers can exhibit various special characteristics depending upon the use that is to be made of the device. For example, some layers can comprise an absorbent material that may be a gel, a hydrogel, a hydrophobic web or a natural or synthetic fibrous material. By way of illustration, the first layer 17, which is here shown as adhesively bonded to surface 14a of the barrier member by a suitable adhesive, can comprise a layer of gauze. Alternatively, the layer can comprise a puncture resistant, protective padding material such as an elastomer which is adapted to protect the user's hands from puncture by sharp articles such as bits of glass and the like. The next layer 18, which is shown as being adhesively bonded to layer 17, can comprise an absorbent powder packet constructed from an absorbent material such as a sponge or fabric pad. Layer 18 here contains a powdered medicament. However, other powdered materials can also be carried by layer 18 including various beneficial agents, disinfectants, drugs and pharmaceuticals of several types. Additional material layers can be interconnected with layer 18, such as a layer which comprises a porous, cellular mass which may, for example, be an elastomer, a sponge, or a polymeric foam. Attached to this layer may be a backing member to which a wound dressing such as hydrogel wound dressing can be affixed in any appropriate manner.

In summary, assemblage 16 can be made up of a wide variety of different types of material so that the device can be used to effectively treat burns, to treat a particular type of wound, to serve as an applicator of topical medications, to clean up numerous types of contamination and to retrieve and safely dispose of various kinds of contaminated articles.

Assemblage 16 can be constructed and arranged to safely deal with a number of different types of contaminants in differing media, including liquids, solids, semi-solids, pastes, micro-organisms, bacteria, viruses, tissue samples and the like.

The protective pouch or barrier member 12 can also be constructed in a number of different ways using a number of different types of materials. For example, the barrier can comprise a single layer of film or a combination of one or more layers of film individually layered or bonded together by heat, adhesive, chemical reaction, or numerous other attachment methods. The film itself can be of various thicknesses and can be of metallic origin, polymeric origin, or it may be nylon, latex, rubber, natural or synthetic composites or any combination of these materials. In summary, the materials used to construct the barrier member can be any material or combination of materials that has the property to substantially limit permeability of liquids, viruses, spores, bacteria, or micro-organisms, so long as it is acceptable for human use and preferably is lint free and flexible under extreme temperature variations. An example of one type of film material suitable for use in constructing the barrier member, is a material made by E. I. duPont de Nemours and Company, and sold under the name and style HYTREL. Another suitable material is a material manufactured and sold by Exxon under the name and style of TPE. Other basic materials acceptable for use in construction of the barrier member for certain applications include neoprene, polyethylene and copolyester films, polypropylenes, polythylenes, polystyrenes, polysophones, polyisopene, polyvinyl, polyamide and numerous polymers including biodegradable polymers such as mylar, latex, nylon, butyl, silicone and acetate. Materials of the character identified should preferably be of a character to provide resistance to penetration and tearing, flexibility in extreme temperature regimes, and, as previously discussed, be micro-organism impermeable. Additionally, for certain applications, it is preferable that the material be transparent or translucent and be substantially resistant to ultraviolet radiation.

It is also understood that the films used to construct the barrier member may be films or components that are coated, or impregnated with one or more chemical or pharmaceutical agents or substances capable of neutralizing or adjusting the acid or pH levels, disinfecting, deodorizing and delivering a pharmaceutical agent to the patient.

With these materials in mind and referring once again to FIG. 3, the first layer 17 can comprise a single layer or a plurality of layers of various types of natural or synthetic materials including materials such as polyester, hydrogel, cotton, rayon, wool, nylon, silicone and like materials. Layer 17 can be bonded to either face or both faces of the barrier member 14 by any suitable means including heat bonding, chemical bonding, adhesive bonding, electrical charge and the like. Similarly, member 18 can be constructed from a wide variety of materials including sponge,elastomers, cellular foam and like cellular structures and can be affixed to assemblage 17 by any suitable means.

Turning once again to FIGS. 3 through 6, the important emergency treatment kit of the invention of which the treatment mits form a part, can be seen to comprise a container 20 having a first body portion 22 defining a first chamber 24 (FIG. 4). Chamber 24 is formed from flexible front and back panels which are suitably interconnected. Stowed within first chamber 24 is a flexible fold-out flap portion 26 (FIG. 6) which has a plurality of individual compartments 28, 30 and 32 for storage of treatment materials and components. Fold-out flap portion can be conveniently stowed within chamber 24 in the manner shown in FIG. 4 and can be unfurled therefrom into a generally planar configuration of the character shown in FIG. 6.

As indicated in FIG. 3, compartment 24 is normally closed by a closure means comprising a top flap 34 which is interconnected with body portion 22 by a zipper 36 mechanism which also forms a part of the closure means. As shown in FIG. 6, flap 34 is preferably hingeably connected along its rearward edge with body portion 22 so that when the zipper 36 is unzipped, flap 34 can be folded into the upward position shown in FIG. 6 thereby permitting easy access to internal chamber 24.

Provided on the front face of first body portion 22 is a front body portion 40 which also has an inner or second chamber 42 that is normally closed by a closure means including an upper flap 44 which is hingeably connected to front body portion 22 and can be opened and closed by a second zipper mechanism 46 which also forms a part of the closure means (FIG. 3).

To enable easy portability of the emergency treatment safety kit, an adjustable carrying strap assembly 50 is interconnected with one of the panels which make up body portion 22 in the manner best seen in FIG. 3. Strap assembly 50 comprises an elongated carrying strap having an adjustable end portion 52, the length of which can be varied by manipulation of a buckle member 54. The carrying strap also includes a second strap portion 56 which is interconnected with strap member 52 by a conventional type of finger release buckle mechanism 58. With this construction, the emergency treatment kit can easily be carried over the user's shoulder, or alternatively, can be carried by hand in the same manner as a small purse.

Various treatment materials and components can be strategically stowed within body portion 22, front body portion 40, and within the compartment of fold-out flap 26. One of the extremely important emergency treatment items stowed within chamber 24 of first body portion 22 is the previously identified treatment mit 12. In the form of the invention shown in the drawings, two treatment mits 12 are stowed within chamber 24 in the rolled up configuration shown in FIG. 4 of the drawings. Each of these treatment mits 12 are of the construction previously described can be conveniently removed from chamber 24 in the manner illustrated in FIG. 5. More particularly, by grasping the open end 12a of the safety mit, the mit can be unrolled and removed from chamber 24 by exerting a force in the direction of the arrow in FIG. 5. With this construction, treatment mits 12 remain in a protected, sterile environment within chamber 24 until time of use.

At the accident site, the safety kit can be removed from the transport vehicle and, using strap assembly 50 can conveniently be carried directly to a location adjacent the accident victim. At this location, access to chamber 24 can be obtained using zipper mechanism 36. Once the zipper mechanism is opened, flap 34 can be moved into a chamber access position and one of the treatment mits 12 can be removed from the chamber in the manner shown in FIG. 5. Once removed from chamber 24, the care giver can insert one hand into interior compartment 14c of the treatment mit and the nit can effectively be used to stop the bleeding of the accident victim or to wipe blood or other body fluids from the patient. Once the engaging means 16 of the mit is saturated, the treatment mit can be turned inside out so as to safely encapsulate the body fluids or other materials which have been absorbed by the engaging means. A convenient tie means or strap 53 is provided proximate opening 14c of the treatment mit in the manner shown in FIG. 1. After the treatment mit has been turned inside out to contain the contaminated materials captured by the on engaging means 16, strip 53 can be removed from the safety mit and used to secure the neck of the treatment mit in a manner to effectively encapsulate the engaging means and contaminants thereon within the interior of the inside out barrier member 14.

Another important treatment component stowed within the emergency kit is a small cardio-pulmonary resuscitation mask 54. As best seen in FIG. 56, pouch or compartment 28 provided on fold-out panel 26 is specially designed to hold the important CPU mask 54. In an emergency situation, once chamber 24 is opened, panel 26 can be removed therefrom and placed in the generally planar configuration shown in FIG. 6. In this configuration, the CPU mask is exposed to view and is readily accessible by the care giver.

Other emergency treatment components such as adhesive tape or the like can be conveniently stowed within compartment 30 while small bandages, gauze and like treatment materials can be stowed within compartment 32.

As illustrated in FIG. 4, still other safety treatment components such as latex gloves, larger bandages, gauze strips and the like can be stowed within compartment 42 of front body portion 40.

With the novel construction of the accident-victim-emergency-treatment kit 20, thus described, the kit can be readily transported to the vicinity of the accident victim. At that location, chamber 24 can be quickly opened by the care giver so as to at once gain access to the treatment mits 12 and to also gain access to fold-out panel 26. By folding panel 26 into the planar configuration shown in FIG. 6, the care giver is given immediate convenient access to additional treatment components such as the CPR mask, adhesive tape and a variety of bandages and other treatment materials. Similarly, the care giver can quickly gain access to chamber 42 of front pouch 40 so as to retrieve therefrom other emergency treatment components such as latex gloves, larger gauze bandages and the like.

In summary, the novel accident-victim-treatment kit of the invention for the first time provides to the care giver a means for treating the accident victim in a prompt, professional manner while at the same time protecting against the spread of infectious disease microorganisms and other contaminants which may be contained within the body fluids of the patient.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A portable treatment, clean-up, transport and disposal apparatus for use by a care giver in rendering medical assistance to a patient, comprising:
    (a) a container including a first body portion defining a first chamber and a fold-out flap portion removably stowed within said first chamber, said fold-out flap portion having a plurality of individual compartments for storage of treatment materials and components; and
    (b) at least one treatment mit carried by said foldable container, said treatment mit comprising:
        (i) a barrier member constructed from a film of material that prohibits the passage therethrough of contaminates, including infectious disease microorganisms, said barrier member having a frontal surface and an interior chamber having an access opening; and
        (ii) engaging means affixed to said frontal surface of said barrier member for engagement with said contaminates and with body fluids of the patient;
        (iii) said barrier member being movable to an inside-out position to enclose therewith said frontal surface and captured contaminates residing thereon.

2. A device as defined in claim 1 further including a CPR mask carried within one of said storage compartments of said flap portion.

3. A device as defined in claim 1 further including a front body portion connected to said first body portion, said front body portion defining a second chamber for storage of treatment materials and components.

4. A device as defined in claim 1 in which said engaging means comprises a plurality of discrete layers of material superimposed over one another.

5. A device as defined in claim 4 in which at least one of said discrete layers carries a medicament.

6. A portable treatment, clean-up, transport and disposal device for use by a care giver in rendering medical assistance to a patient, comprising:
    (a) a container comprising:
        (i) interconnected flexible front and back panels cooperating to define a first chamber;
        (ii) a flexible fold-out panel connected to a selected one of said front and back panels, said fold-out panel being movable from a stowed position within said first chamber to a folded out, generally planar configuration, said fold-out panel having first and second compartments;
    (b) a CPR mask removably contained within one of said first and second compartments;
    (c) a patient treatment component removably contained within one of said first and second compartments; and
    (d) at least one treatment mit carried within said first chamber, said treatment mit comprising;
        (i) a seamless, flexible, non-latex, hypoallergenic barrier member defining an enclosure having an access opening, said barrier member being constructed from a material that prohibits passage therethrough of blood and body fluids; and
        (ii) at least one layer of an absorbent material connected to said barrier material.

7. A device as defined in claim 6 further including a front body portion connected to said front panel of said container, said front body portion having a second chamber.

8. A device as defined in claim 6 further including an adjustable carrying strap assembly connected to said container.

9. A device as defined in claim 6 in which said absorbent material of said treatment mit comprises a layer of gauze.

10. A device as defined in claim 6 in which said absorbent material of said treatment mit comprises a sponge.

11. A device as defined in claim 6 in which said absorbent material of said treatment mit comprises a laminate construction made up of a layer of sponge and a layer of gauze.

12. A device as defined in claim 6 in which said container further comprises closure means connected to said flexible front and back panels for closing said first chamber.

13. A device as defined in claim 6 in which two treatment mits are carried within said first chamber in a rolled configuration.

14. A portable treatment, clean-up, transport and disposal device for use by a care giver in rendering medical assistance to a patient, comprising:
    (a) a container comprising:
        (i) interconnected flexible front and back panels cooperating to define a first chamber;
        (ii) a flexible fold-out panel connected to a selected one of said front and back panels, said fold-out panel being movable from a stowed position within said first chamber to a folded out, generally planar configuration, said fold-out panel having first and second compartments;
        (iii) a front storage container connected to said first panel, said front body portion, having a second chamber; and
        (iv) an adjustable carrying strap assembly connected to a selected one of said front and back panels;
    (b) a CPR mask removably contained within one of said first and second compartments;
    (c) a patient treatment component removably contained within one of said first and second compartments; and
    (d) at least one treatment mit carried within said first chamber, said treatment mit comprising;
        (i) a seamless, flexible, non-latex, hypoallergenic barrier member defining an enclosure having an access opening, said barrier member being constructed from a material that prohibits passage therethrough of blood and body fluids; and
        (ii) an absorbent material connected to said barrier material, said absorbent material comprising a sponge layer and a gauze layer.

15. A device as defined in claim 14 in which said foldable container further comprises closure means connected to said flexible front and back panels for closing said first chamber.

16. A device as defined in claim 15 in which two treatment mits are carried within said first chamber in a rolled configuration.

17. A device as defined in claim 16 in which each of said two treatment mits include tie means for closing said access opening thereof.

* * * * *